United States Patent [19]
Moran

[11] Patent Number: 6,113,528
[45] Date of Patent: Sep. 5, 2000

[54] NEEDLE MANIPULATION RULE

[76] Inventor: Brian J. Moran, 604 E. 1st St., Hinsdale, Ill. 60521

[21] Appl. No.: 09/095,850

[22] Filed: Jun. 10, 1998

[51] Int. Cl.[7] .............................. A61N 5/00; A61M 36/00
[52] U.S. Cl. ..................................................... 600/7; 600/1
[58] Field of Search ............................ 600/1–8; 128/587; 33/483–494

[56] References Cited

U.S. PATENT DOCUMENTS

| | | | |
|---|---|---|---|
| 363,331 | 5/1887 | Hammer | 33/483 |
| 419,268 | 1/1890 | Low | 33/483 |
| 1,183,039 | 5/1916 | Schoeneberger | 33/483 |
| 1,877,342 | 9/1932 | Kurtz, Jr. | 33/492 |
| 2,579,664 | 12/1951 | Gleasman | 33/492 |
| 4,086,914 | 5/1978 | Moore et al. | 600/7 |
| 4,462,168 | 7/1984 | Lynch et al. | 33/492 |
| 4,654,976 | 4/1987 | Diawan | 33/485 |
| 5,083,380 | 1/1992 | Robertson | 33/486 X |
| 5,295,945 | 3/1994 | Miller . | |
| 5,328,479 | 7/1994 | Gurmarnik . | |
| 5,498,227 | 3/1996 | Mawad . | |
| 5,562,594 | 10/1996 | Weeks . | |
| 5,688,220 | 11/1997 | Verin et al. . | |
| 5,728,042 | 3/1998 | Schwager . | |
| 5,771,598 | 6/1998 | Lassberg | 33/494 |
| 5,860,909 | 1/1999 | Mick et al. | 600/7 |

OTHER PUBLICATIONS

"Prostate Implant Accessories". Standard Imaging web site at www.standarimaging.com. printed May 12, 1998.

*Primary Examiner*—Samuel G. Gilbert
*Attorney, Agent, or Firm*—Mayer, Brown & Platt

[57] ABSTRACT

A needle manipulation ruler for use in brachytherapy allowing a needle containing radioactive material to be manipulated without exposing the surgeon to radioactivity. A plurality of needle engagers are contained on the needle manipulation ruler. These needle engagers can be indentations in the needle manipulation ruler or protuberances on the needle manipulation ruler. A needle can be engaged with the needle engagers by either inserting the needle into the indentations or pressuring the needle against the protuberances. The engaged needle can be adjusted in any direction from any angle that the needle manipulation ruler is held relative to the needle.

7 Claims, 3 Drawing Sheets

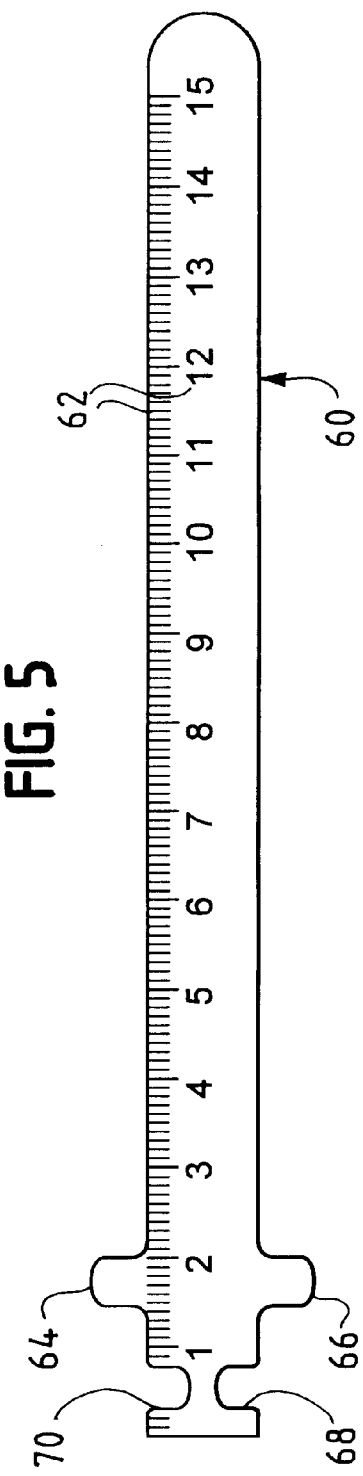
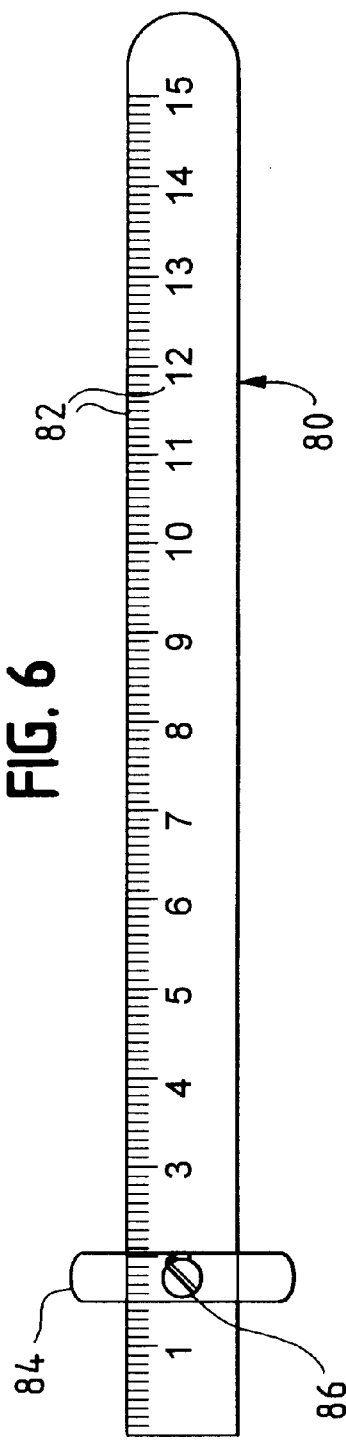

NEEDLE MANIPULATION RULE

BACKGROUND OF THE PREFERRED EMBODIMENT

1. Field of the Preferred Embodiment

This invention relates generally to a medical device and more particularly to medical device used to manipulate a radioactive needle in surgical procedures such as brachytherapy.

2. The Prior Art

It is well known in the art to use brachytherapy to treat prostate cancer. Reports date back to the early 1900s of brachytherapy being used in the treatment of prostate cancer. Radium needles were initially used, however this was abandoned over time because of radiation exposure to the hands of the surgeon, as well as the fact that radium is not an ideal isotope for such a procedure. In the 1970s, the use of iodine-125 was performed using a suprapubic open surgical technique. This procedure proved unsuccessful and it was abandoned in the early 1980s. In 1993, after the development of the transrectal ultrasound, brachytherapy once again surfaced in the treatment of prostate cancer.

Using a transperineal approach and the use of a template, needles are inserted into the prostate in an exact fashion. The results of this procedure have proven successful, and prostate brachytherapy is now one of the preferred treatments in the management of early-stage prostate cancer.

In brachytherapy treatment of prostate cancer, transrectal ultrasound is used to visualize the prostate. The patient is then implanted with radioactive seeds using twenty (20) centimeter long, 18-gage needles to deposit radioactive iodine-125 or palladium-103 radioactive seeds. These seeds are distributed through the prostate evenly, resulting in a uniform dose of radiation.

The physical characteristics of iodine-125 and palladium-103 are much superior to radium or other isotopes for the purpose of permanent implantation in the prostate gland. The radiation energy is quite low and has a limited exposure rate to the body structures located around the prostate. However, the needles themselves, when filled with radioactive isotopes, do exhibit significant radiation exposure at the surface of the needle and up to a distance of six (6) centimeters. Therefore, if the surgeon's hands or fingers come within a six (6) centimeter radius of the needle, the surgeon will be exposed to radiation. Such exposure is undesirable.

In the past, surgeons have used a fifteen (15) to twenty (20) centimeter stainless steel ruler to assess the depth of needle insertion into the prostate gland. This is a useful aid in exact implantation of the prostate. To control the direction of insertion of the needle once the needle is inside the patient, surgeons have used their fingers to guide and manipulate the needle. Significant exposure to radiation can result to the fingers and hands of the surgeon while touching the needle that houses the radioactive seeds prior to deposition in the prostate gland.

SUMMARY OF THE PREFERRED EMBODIMENT

The present invention is a medical device for use in brachytherapy that minimizes the surgeon's exposure to radiation while still allowing the surgeon to properly guide and manipulate the needle inside the patient. With a series of needle engagers contained on the end of a needle manipulator, the surgeon is able to manipulate the needle into its proper location without physically touching the needle with his or her fingers or hand. The needle engagers are shaped and positioned to allow the needle to be adjusted in any direction from any position relative to the needle manipulator. The advantage of using the needle manipulator is that the surgeon's exposure to radiation while using the needle manipulator is greatly reduced when compared to using the surgeon's fingers to adjust the ruler. A further advantage of using the needle manipulator is that the surgeon is able to more accurately adjust the needles than when using his or her fingers.

By integrating a ruler into the needle manipulator, the surgeon has a single device that can be held in one hand and used to safely manipulate the needle and measure the depth of insertion of the needle into the prostate gland rather than having to work with two separate devices.

These and other features and advantages of the invention will be apparent upon consideration of the following detailed description of the preferred embodiments of the invention, taken in conjunction with the appended drawings.

BRIEF DESCRIPTION OF THE DRAWINGS

FIG. 5 is a diagram of an alternate embodiment of a needle manipulation ruler in accordance with the invention.

FIG. 6 is a diagram of an alternate embodiment of a needle manipulation ruler in accordance with the invention.

DETAILED DESCRIPTION OF THE PRESENTLY PREFERRED EMBODIMENTS

Figure 1:
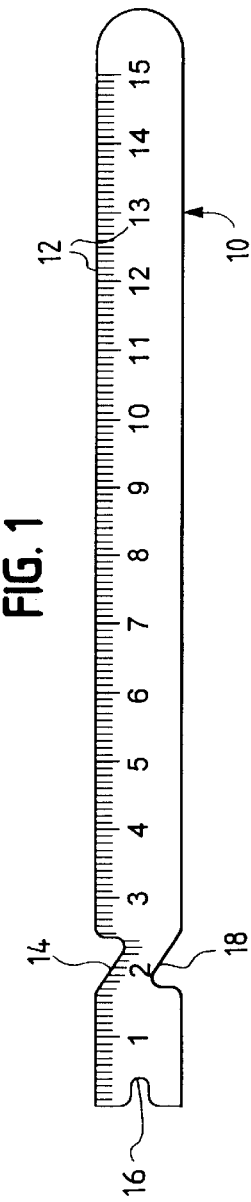
FIG. 1 is a diagram of a preferred embodiment of a needle manipulation ruler in accordance with the invention.

Referring to FIG. 1, a needle manipulator 10 is shown. The needle manipulator 10 preferably is made of stainless steel, but can be made of plastic or any other material that is suitable to be sterilized such that it can be used in a surgical procedure. Units of measurement 12 are placed on the needle manipulator 10. In a preferred embodiment, a plurality of needle engagers 14, 16, and 18 are formed on the needle manipulator 10. These needle engagers 14, 16 and 18 are indentations in the needle manipulator 10 into which a needle can be inserted and adjusted in any direction from any angle that the needle manipulator 10 is held relative to the needle. The needle manipulator 10 is preferably fifteen (15) centimeters long, but can be any length sufficient to keep the surgeon's fingers and hands outside of the radioactive energy released by the needle. Thus, the needle manipulator 10 preferably should be at least ten (10) centimeters long.

Note that, as used herein, the term "needle engager" is defined to include either an indentation in the needle manipulator into which the needle will fit and can be adjusted, a protuberance on the needle manipulator against which the needle can be pressured and adjusted, or a combination of the two.

Figure 4:
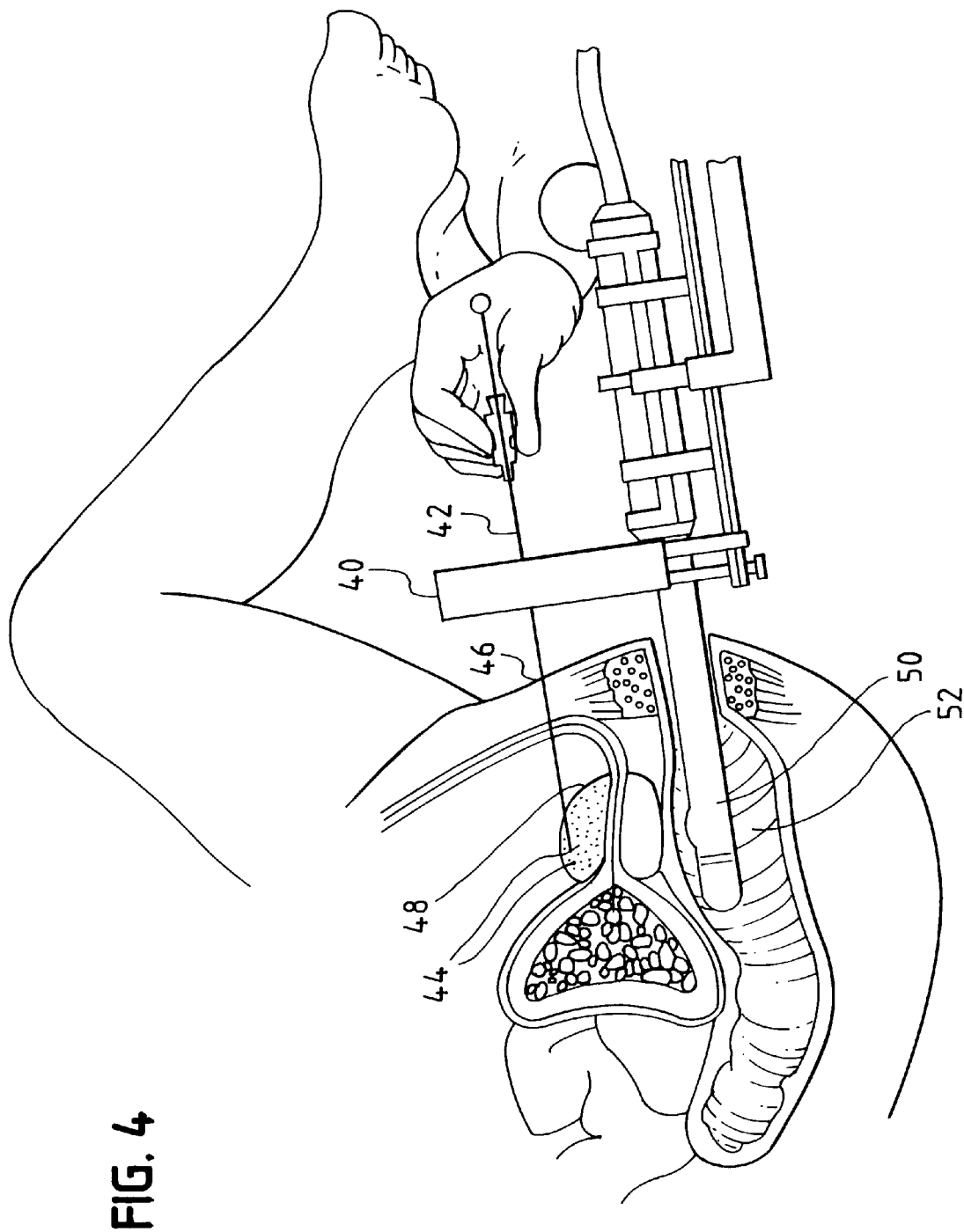
FIG. 4 is a diagram of a surgical procedure using brachytherapy in which the needle manipulation ruler is used.

Referring to FIG. 4, a brachytherapy procedure used to treat prostate cancer is shown. A needle guide 40 is fixed relative to the patient through which a needle 42 containing radioactive seeds 44 is placed. The needle 42 is then inserted into the patient through the patient's skin 46 and into the patient's prostate gland 48. Separately, an ultrasonic probe 50 is placed into the patient's rectum 52. The ultrasonic probe 50 projects an image of the patient's prostate gland 48 onto a television receiver (not shown). The surgeon can determine whether the needle 42 is in the proper position in the patient's prostate gland 48 by viewing the ultrasonic image projected onto the television receiver. If the needle 42 is not in the proper position, the surgeon partially removes the needle 42 and adjusts the position of the needle 42 using the needle manipulator 10. The needle 42 is adjusted by placing pressure on the needle 42 by inserting the needle 42 into one of the needle engagers on the needle manipulator 10 as the needle 42 is reinserted. The surgeon can then use the needle manipulator 10 to measure how far the needle 42 is inserted into the patient to ensure proper depth of insertion into the prostate gland 48.

The above process is repeated until the needle 42 is in the proper position within the patient's prostate gland 48. After the needle 42 is in the proper position, the surgeon removes the needle 42 from the patient while leaving the radioactive seeds 44 within the patient's prostate gland 48 in manner that is well known in the art.

Figure 2:
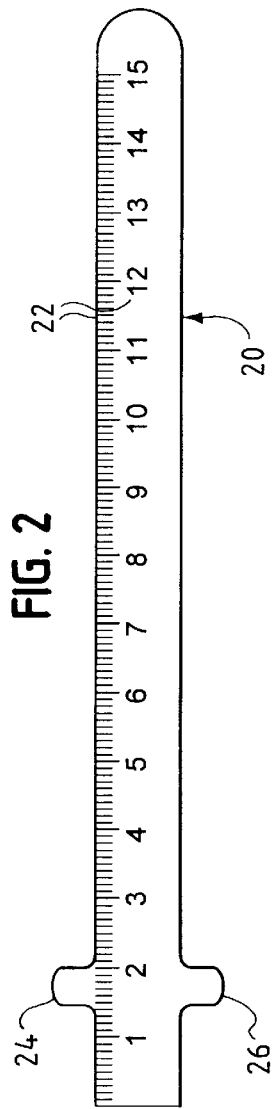
FIG. 2 is a diagram of an alternate embodiment of a needle manipulation ruler in accordance with the invention.

Referring to FIG. 2, an alternate embodiment of the present invention is shown. A needle manipulator 20 preferably is made of stainless steel, but can be made of plastic or any other material that is suitable to be sterilized such that it can be used in a surgical procedure. Units of measurement 22 are placed on the needle manipulator 20. A plurality of needle engagers 24 and 26 are formed on the needle manipulator 20. These needle engagers 24 and 26 are protuberances on the needle manipulator 20 against which a needle can be pressured. By pressuring the needle against needle engagers 24 and 26, the needle can be adjusted in any direction from any angle that the needle manipulator 20 is held relative to the needle.

Figure 3:
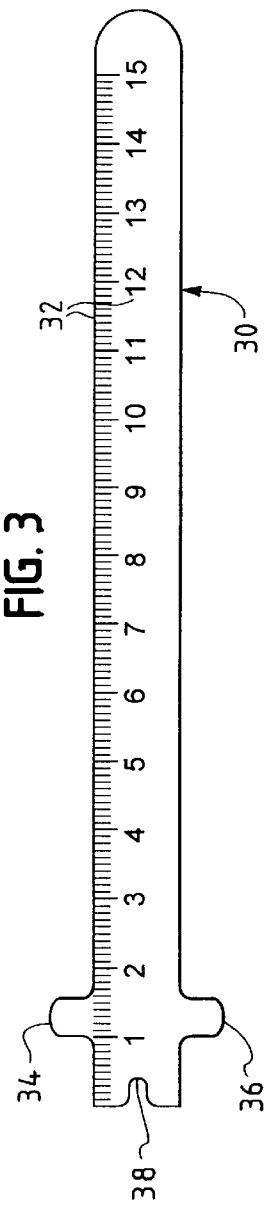
FIG. 3 is a diagram of an alternate embodiment of a needle manipulation ruler in accordance with the invention.

Referring to FIG. 3, an alternate embodiment of the present invention is shown. A needle manipulator 30 preferably is made of stainless steel, but can be made of plastic or any other material that is suitable to be sterilized such that it can be used in a surgical procedure. Units of measurement 32 are placed on the needle manipulator 30. A plurality of needle engagers 34, 36 and 38 are formed on the needle manipulator 30. Needle engagers 34 and 36 are protuberances on the needle manipulator 30 against which a needle can be pressured. By pressuring the needle against needle engagers 24 and 26, the needle can be adjusted in any direction from any angle that the needle manipulator 20 is held relative to the needle. Needle engager 38 is an indentation in the needle manipulator 30 into which a needle can be inserted and adjusted.

Any number and any combination of protuberances and indentations can be used in accordance with the present invention to allow manipulation of a needle in any direction. For example, referring to FIG. 5, a needle manipulator 60 having units of measure 62 and a plurality of needle engagers 64, 66, 68 and 70 is shown. The needle manipulator 60 can be made of the same materials discussed above. Needle engagers 64 and 66 are protuberances on the needle manipulator 60 against which a needle can be pressured. Needle engagers 68 and 70 are indentations in the needle manipulator 60 into which a needle can be inserted and adjusted.

Furthermore, the protuberances can be integrally formed in the needle manipulator or can be formed as separate pieces and affixed to the ruler. For example, referring to FIG. 6, a needle manipulator 80 having units of measure 82 and a moveable needle engager 84 is shown. The needle manipulator 80 can be made of the same materials discussed above. Moveable needle engager 84 creates protuberances on the needle manipulator 80 against which a needle can be pressured. The moveable needle engager 84 can be adjustably attached to the needle manipulator 80, for example by using a screw 86, so the surgeon can move the protuberances to any desired position on the needle manipulator 80.

It is to be understood that a wide range of changes and modifications to the embodiments described above will be apparent to those skilled in the art and are contemplated. It is, therefore, intended that the foregoing detailed description be regarded as illustrative rather than limiting, and that it be understood that it is the following claims, including all equivalents, that are intended to define the spirit and scope of the invention.

What is claimed is:

1. A method of manipulating a needle after the needle has been inserted into a body of a patient using a needle manipulator comprising:

partially removing the needle from the body of the patient;

engaging the needle with the needle manipulator; and reinserting the engaged needle into the body of the patient while applying pressure to the engaged needle using the needle manipulator.

2. The method of claim 1, wherein the needle manipulator includes one or more needle engagers.

3. The method of claim 2, wherein the needle engagers comprise one or more indentations in the needle manipulator.

4. The method of claim 3, wherein the needle is engaged by inserting the needle into one of the indentations in the needle manipulator.

5. The method of claim 2, wherein the needle engagers comprise one or more protuberances on the needle manipulator.

6. The method of claim 5, wherein the needle is engaged by pressuring the needle against one of the protuberances on the needle manipulator.

7. The method of claim 1, further comprising measuring the distance the needle has been inserted into the body using the needle manipulator.

* * * * *